(12) United States Patent
Graf

(10) Patent No.: US 10,370,007 B2
(45) Date of Patent: Aug. 6, 2019

(54) INSPECTION AND MONITORING SYSTEM FOR A CABLE RAILWAY AND A METHOD OF OPERATING THE SAME

(71) Applicant: FATZER AG DRAHTSEILFABRIK, Romanshorn (CH)

(72) Inventor: Daniel Graf, Balgach (CH)

(73) Assignee: Fatzer AG Drahtseilfabrik, Romanshorn (CH)

( * ) Notice: Subject to any disclaimer, the term of this patent is extended or adjusted under 35 U.S.C. 154(b) by 170 days.

(21) Appl. No.: 15/097,384

(22) Filed: Apr. 13, 2016

(65) Prior Publication Data

US 2016/0297455 A1 Oct. 13, 2016

(30) Foreign Application Priority Data

Apr. 13, 2015 (CH) ........................ 0521/15

(51) Int. Cl.
*B61L 23/04* (2006.01)
*B61B 7/00* (2006.01)
(Continued)

(52) U.S. Cl.
CPC .............. *B61B 7/00* (2013.01); *B61B 12/06* (2013.01); *G01N 27/82* (2013.01); *G01N 27/83* (2013.01); *G01N 29/04* (2013.01)

(58) Field of Classification Search
CPC .......... B61B 7/00; G01N 27/83; G01N 27/82; G01N 29/04
See application file for complete search history.

(56) References Cited

U.S. PATENT DOCUMENTS

| 4,538,107 | A | * | 8/1985 | Varone | .................. | G01N 27/82 324/206 |
| 5,565,771 | A | * | 10/1996 | Hamelin | ................ | G01N 27/82 324/225 |

(Continued)

FOREIGN PATENT DOCUMENTS

| CN | 203502379 U | 3/2014 |
| EP | 0134341 A1 | 3/1985 |

(Continued)

OTHER PUBLICATIONS

Abstract of CN 203502379U.

*Primary Examiner* — Xin Y Zhong
(74) *Attorney, Agent, or Firm* — Brian Roffe

(57) ABSTRACT

Inspection and monitoring system consists of a measuring unit fixedly installed in the cable railway, a storage and transmission unit operatively connected to the latter for the storage and communication of the measurement data, and an assessment unit connected to the latter via Ethernet or some comparable network in order to assess and visualize the measurement data in a remote monitoring station away from the cable railway from which the inspection process is initiated automatically according to a set program. Assessment of the inspection results in the remote monitoring station also takes place automatically by means of a pre-specified program. The station can be in operation around the clock and can also monitor a number of cable railways a long way away at the same time. It works reliably without staff interaction and enables precise management of the cable in view of its optimal life span.

19 Claims, 1 Drawing Sheet

(51) Int. Cl.
*G01N 29/04* (2006.01)
*G01N 27/82* (2006.01)
*G01N 27/83* (2006.01)
*B61B 12/06* (2006.01)

(56) References Cited

U.S. PATENT DOCUMENTS

| | | | | |
|---|---|---|---|---|
| 2006/0247868 A1* | 11/2006 | Brandstrom | ........... | G01N 27/82 |
| | | | | 702/35 |
| 2007/0168159 A1* | 7/2007 | Veronesi | ............... | B66B 7/1223 |
| | | | | 702/182 |
| 2008/0314129 A1* | 12/2008 | Schultz | ................. | G01N 30/80 |
| | | | | 73/61.55 |
| 2009/0194390 A1* | 8/2009 | Freeman | ................ | B65G 43/02 |
| | | | | 198/810.01 |
| 2015/0285767 A1* | 10/2015 | Ouellette | ............... | G01R 33/04 |
| | | | | 324/240 |

FOREIGN PATENT DOCUMENTS

| | | |
|---|---|---|
| EP | 1995589 A2 | 11/2008 |
| WO | 2013055196 A1 | 4/2013 |

\* cited by examiner

INSPECTION AND MONITORING SYSTEM FOR A CABLE RAILWAY AND A METHOD OF OPERATING THE SAME

FIELD OF THE INVENTION

The invention relates to an inspection and monitoring system for a cable railway, in particular for the urban transportation of people and goods, and to a method of operating the latter.

BACKGROUND OF THE INVENTION

Cable railways are being used more and more frequently, especially in cities, as a substitute for over- or underground metropolitan railways. They offer the advantage that they can be integrated into the town relatively independently of topography and existing buildings and infrastructure, and so can transport people and goods quickly as an independent traffic system. They connect two or more points over the respectively shortest possible route—the air line. Such cable railways are normally linked into the public transport networks and operate without interruption for up to 20 hours a day. The resulting high stress to which the cable and components of the cable railway system are subjected due to the large number of cable revolutions causes comparably accelerated material fatigue and increased wear, and so in urban systems, in contrast to, for example, mountain railways, the criteria for discarding cables are met considerably earlier, often after just a few years of operation.

However, operating failures are very undesirable and, in addition, are expensive, especially as in urban systems they generally result in an interruption of the public transport system. Work on the cable, for example cable shortening, splice renovation, repair work or also the replacement of a cable, is time-consuming and so must be planned in good time in order to minimize disruption to the regular cable railway operation. In addition, there is often the problem that when fitting a new cable there is too little free space for the joining of a revolving cable by splicing, and in towns this can even lead to roads or squares having to be blocked in order to be able to carry out the splicing work.

In order to recognize the discard state or the end of the life span of a cable, standardized discard criteria are applied. These standards, which are often country-specific, also prescribe the inspection intervals within which the cable must be inspected by an authorized test center, e.g., by means of magnetic test methods. Depending on the state of the cable and the anticipated number of bending cycles within a specific period of time, the inspection interval is reduced by the expert, and it is thus ensured that a follow-up inspection will be carried out before a critical state occurs.

For conventional mountain railways with a relatively short daily operating period and/or seasonally limited operation and so an accordingly small number of bending cycles per year, the inspection interval can be extended to a maximum if the cable is in a good state. Running cables (revolving cables or cables in reversing operation) of such systems can achieve life spans in the order of over 20 years depending on the operating conditions.

In urban cable railway systems, the inspection interval must be considerably reduced on the basis of the much longer daily operating period and operation throughout the year and the resulting large number of bending cycles. The period of use of a running cable in an urban system, i.e., the time until the discard state has been reached, can even be shorter than the maximum inspection interval. The inspection cycles must also be set to less than a year, depending on the state of the cable, in order to ensure that the discard state can be recognized.

In addition to the inspection of the cable by an expert, visual inspections are prescribed that must be carried out by the operator itself. This type of visual check is carried out with the human eye or can be backed up by technical systems.

OBJECTS AND SUMMARY OF THE INVENTION

In contrast, the object underlying the invention is to devise an inspection and monitoring system for a cable railway and a method of operating the latter, by means of which an optimal design of this cable railway, and in particular also of the cable, and furthermore increased safety of the system overall is achieved. Within this context cable inspections should be carried out on running cables within short intervals and in this way a rapid assessment of the current state of the cable is made possible.

According to the invention, this object is achieved by an inspection and monitoring system for a cable railway including a cable guided from one end to the other of the cable railway and which advances the one or more cabins or trains, and wherein the inspection and monitoring system is connected to an assessment unit and enables the monitoring and inspection of at least the cable. The method involves such an inspection and monitoring system wherein an operating state of the cable is determined by online testing of the cable with preferably electromagnetic signals.

Highly stressed cable railway systems in particular, such as urban systems and/or systems with extremely large numbers of bending cycles, should acquire a greater level of safety by means of regular inspection at short intervals. Moreover, more or less permanent monitoring and detection of the state of the cable enables forward planning for necessary work on the cable, and in this way operational interruptions are minimized and scheduling that is optimal for operation is made possible. By means of a life span prediction based on a plurality of measurements, unanticipated failure of a cable should be prevented as far as is possible.

In this way one primarily determines the splicing point for the cable which is known to be structurally more heterogeneous and/or stronger than the cable line. The positioning of the splicing point makes it possible to count the rotations executed by the cable line, and so to determine the cable path covered between two consecutive measuring cycles. However, it also makes it possible to precisely locate any parts of the cable that are damaged in relation to the previously located splicing point.

For the management of the cable in view of an optimal life span of the cable the invention makes provision such that the inspection results are assessed taking into account certain parameters that describe and influence the operating state of the system, such as the number of bending cycles and the length of the cable path covered. These parameters can also optionally include the lay length of the cable and/or the change in position of the tension carriage re-tensioning the cable, as well as the ambient temperature, the noise emission of the system e.g. caused by the increasing vibration due to the wear of system parts and/or the air properties in the system.

The on-line inspection of the cable enables automatic implementation of the inspection and assessment according to a previously determined monitoring program that takes into account the aforementioned parameters and any other input, such as the number of splices and/or the overall cable length.

Since frequent inspection of the system is required for the management of the cable of a highly stressed cable railway system, the invention makes provision such that the inspection process is initiated automatically by the monitoring program with a pre-specified short frequency, for example weekly, and/or at a pre-specified date.

According to the invention, it is possible to activate the test apparatus both automatically from the remote monitoring station and in situ by means of an actuation button attached to the apparatus.

The inspection and monitoring system according to the invention that generally works independently of the cable railway operation consists of a measuring unit installed in the cable railway, a storage and transmission unit adjacent to the latter here, and an assessment unit installed in the remote monitoring station and that has assessment and analysis software for assessing and visualising the measurement data communicated from the storage and transmission unit via Ethernet or other networks. This inspection and monitoring system can also be retrofitted to existing systems.

The inspection system can also be used in combination with other inspection methods. It is therefore possible, e.g. to carry out a visual check with the aid of a visual test apparatus at the same time as the magnetic test by means of the permanently installed inspection system. The time required to carry out these tests is minimized because both tests can take place in the same cycle.

The measuring unit consists of a magnetization unit and a sensor system that covers the cable.

The magnetization unit magnetizes the cable with the aid of permanent magnets or electromagnets. The cable magnetized by the magnetization unit emits a stray magnetic field that is detected by the sensor system.

The sensor system consists of one or more coils or Hall sensors that are arranged around the cable. There are therefore at least 2 measuring principles that can also be used in combination. Measurement with coils is based on the magnetic voltage induction by the relative movement between the coil and the magnetized cable. A voltage is induced in the coil(s) by the stray magnetic field of the magnetized cable. The measurement with Hall sensors is based on the so-called Hall effect. The voltage on the Hall sensor changes depending on the magnetic field strength of the magnetized cable.

The stray magnetic field of the cable can therefore be detected by the sensor system. Defects in the cable such as e.g. wire breakages also cause a stray magnetic field which overlays the stray magnetic field of the cable and is detected by the sensor system. Depending on the cable and the nature of the defect, a typical measuring signal is generated. The measuring signal is finally made available for assessment.

The measuring system can record the cable meters that have been travelled and makes these available for assessment. Automated calculation of the number of bending cycles can take place. The cable meters travelled can be detected by the sensor system or with additional external sensors.

Within the framework of the invention it is also possible to integrate the components of the system installed in the cable railway, namely the measuring unit and the storage and transmission unit, into an apparatus.

BRIEF DESCRIPTION OF THE DRAWINGS

The invention will be described in more detail in the following by means of an exemplary embodiment with reference to the drawings. These show as follows.

DETAILED DESCRIPTION OF THE INVENTION

Figure 1:
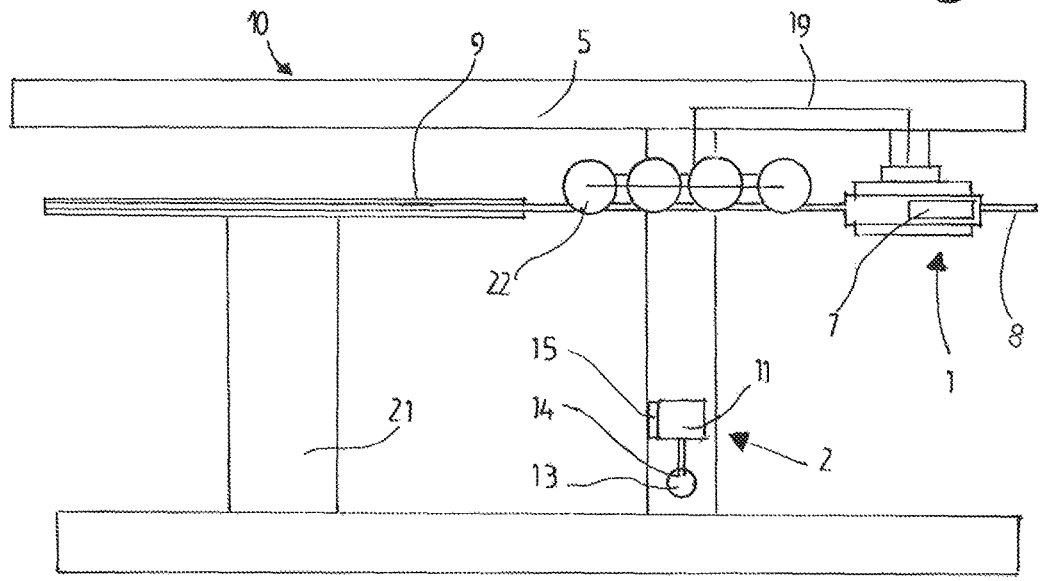
FIG. 1 is a diagrammatic view of the end of a cable railway with the components of an investigation and monitoring system according to the invention.

FIG. 1 shows diagrammatically the end of an urban cable railway 10 which, in the present exemplary embodiment, is in the form of an aerial cable railway. This type of aerial cable railway is installed in particular in an urban area. It thus makes it possible to transport people and goods quickly and independently of the roads, and so also only causes a small amount of noise. However, one can also provide a cable railway on rails which is also primarily installed in towns.

Of this cable railway 10 the circulating roller 9 at the end rotatably mounted on a stand 21 and guide rollers 22 for the cable 8 are illustrated. This circulating roller 9 can also be made in the form of a drive wheel. The cable 8 is guided here from one end to the other of the cable railway 10 and advances the cabins which are released from the cable 8 at the stations and are consequently not illustrated.

According to the invention, an inspection and monitoring system 1, 2 is preferably integrated at the end of the cable railway 10 which is connected to an assessment unit 4 and enables the monitoring and inspection of at least the cable 8.

Advantageously, a measuring unit 1 of the inspection and monitoring system at the end of the cable guide is fastened to the station support 5 and its test apparatus 7 encompasses the cable or is disposed directly next to the cable. A storage and transmission unit 2 advantageously connected to this measuring unit 1 via a data line 19 is connected to the assessment unit 4 via Ethernet or some similar data network and via a network. The free section of cable to which the test apparatus 7 is fitted is advantageously located close to the circulating roller 9 and, in order to avoid false measurements, ideally where no cabins are suspended.

With this cable railway according to the invention, improvements can be achieved both as regards the operational reliability of the system and the economic efficiency of the system operation over the longest possible operating period.

The measuring unit 1 is provided with a test apparatus 7 that is installed fixedly and the magnetic field of which acts on the cable 8 such that a current is conveyed through a coil placed about the cable without any contact, the voltage of which current is dependent upon the strength of the magnetic field according to the so-called Hall effect and so generates signals that are dependent upon deviations in the strength and/or properties of the cable.

The measuring unit 1 includes a magnetization unit that brings about magnetization of the cable 8. The stray magnetic field of the cable is detected by the sensor system of the measuring unit that is also integrated into the measuring unit. The sensor system consists of one or more coils or a number of Hall sensors or a combination of coil(s) and Hall sensors which encompass the cable without any contact. The stray magnetic field of the cable is detected by the sensor system. A typical measurement signal is generated dependently upon the cable and the properties of a defect and is made available for the assessment.

The storage and transmission unit 2 is installed close to the measuring unit 1 and is operatively connected to the latter by means of this data line 19. The storage and transmission unit 2 includes a storage part 11 and a data transmission part 12, a mains connection 13 and an Ethernet connection 14 by means of which the connection to the monitoring station or center 3 is established. The storage part 11 can also be provided with a port 15 for a USB stick. The storage part 11 must be able to store a number of complete measurements of a cable, and the stored data must also be retained if there is a power failure.

Instead of a cable-bound network connection, a cable-free connection to a network can also be integrated into the storage and transmission unit 2, which connection enables a radio connection or mobile radio connection to a network, and so contact to the assessment unit 4.

The measuring unit 1 is fixedly installed in a support 5 of the cable railway and includes a bending cycle counter 6 and the test apparatus 7 with the associated hardware, the magnetic field of which acts on the cable such that a current is conveyed within a coil placed around the cable without any contact, the voltage of the current depending on the magnetic field strength resulting from the cross-section and properties of the cable. The resulting electromagnetic signals are stored in the storage and transmission unit 2 and are transmitted here to the assessment unit 4.

Figure 2:
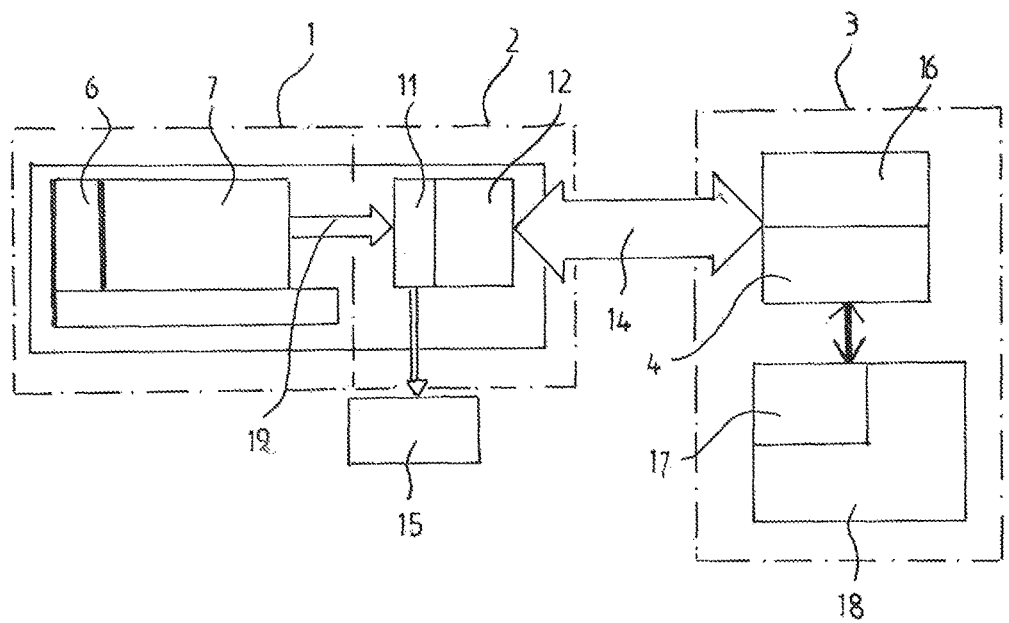
FIG. 2 is a block diagram of the inspection and monitoring system of the cable railway according to FIG. 1.

According to FIG. 2, this inspection and monitoring system comprises this measuring unit 1, the storage and transmission unit 2 for storing and communicating the measurement data, and this assessment unit 4 for assessing and visualizing the measurement data. The assessment unit 4 is on its part accommodated away from the cable railway in a monitoring station or center 3. Here, the processing and assessment of the measurement data communicated via the network can be carried out permanently or at certain intervals of time.

The starting point for the measurement is always at the same point of the cable, this point being recognized automatically by the test apparatus 7. The starting point preferably serves as the splicing point of the cable which, at the same time, is used as the reference point for the positioning of the other testing points.

In order to determine the number of bending cycles the path of the cable movement along its axis covered by the cable railway during operation is measured. This cable path is stored, for example, in the diurnal rhythm and should advantageously come within the required values for an optimal life span of the cable.

In the exemplary embodiment described the units 1 and 2 are two components of the system that are separated from one another as regards apparatus. Within the framework of the invention they can however easily be packed within a single piece of apparatus.

The assessment unit 4 is located away from the cable railway in the remote monitoring station or center 3 which also contains a device 16 for standard settings and is provided with a software program 17 for assessment, analysis and visualization by means of a PC system 18. The basic settings to be input include the number of splices and the respective cable length. These basic settings can be changed via Ethernet each time there is remote access. The assessment unit 4 also makes forecasts with regard to the life span of the cable for the free cable length or for the life span of the splice by means of the bending cycles counted.

The assessment unit 4 also has visualization software for the optical display of measurement data including the graphical processing of results and in particular of any wire breakages that occur.

The inspection in the monitoring station or center 3 is generally initiated automatically each time there is remote access according to a set program according to which the frequency, the day of the week and the time of the measurement are specified. However, in special cases, the inspection can also be initiated in situ by actuating an actuation button disposed on the test apparatus 8. Additional remote access to the test apparatus 8 makes it possible to read out the memory.

The subsequent assessment of the measurement data also takes place automatically in the unit 17, 18 of the monitoring station or center 3 by means of a program that takes into account a series of parameters such as the number of bending cycles, the number of splices and the overall cable length as well as the ambient temperature in the system, the lay length of the cable and the position of the tension carriage re-tensioning the cable in order to increase the informative value of the test results. It is advantageous to integrate this type of tension carriage into the stand 21, but this is not detailed. This tension carriage causes the cable 8 guided around the roller 9 to be tensioned with a predetermined force against its longitudinal extension.

One may also include measurement results from other comparable cable railways which are also monitored from the monitoring station or center 3. The control programs can be set individually from case to case.

The inspection and monitoring system according to the invention makes it possible to regularly inspect the cable railways with an apparatus-qualified device which works instantaneously and reliably without any staff interaction. It also enables the central remote monitoring of a number of cable railways, the locations of which are a long way away from one another.

The system offers significant advantages as regards apparatus, staff and cost-effectiveness and, moreover, enables the precise management of the cable in view of an optimal life span. One can also achieve improvements with regard to the operational reliability of the system and the cost-effectiveness of the system operation over the longest possible operating period.

Furthermore, very reliable location and detection of the splicing point can also be achieved by measuring acoustic values and/or vibrations of the running wire cable. By means of a measuring device, that is not detailed, these acoustic values can be determined by a microphone or by a vibration sensor which can be fitted somewhere on the system, and be correspondingly assessed.

The inspection system and the described method can be used universally for running cables and so can also be retrofitted to existing systems.

Furthermore, the test method can be used in combination with other cable inspection methods, such as e.g. electronically supported visual cable inspection.

The invention claimed is:

1. An inspection and monitoring arrangement for a cable railway, comprising:
   a cable guided between ends of the cable railway and which advances one or more cabins or trains, the cable having at least one splicing point and a known cable length,
   an inspection and monitoring system that monitors and inspects the cable and is integrated into the cable railway, the inspection and monitoring system comprising:
      a measuring unit that measures the cable and obtains measurement data, the measuring unit being installed in connection with the cable railway, the measuring unit including a bending cycle counter such that the measurement data includes data from the bending cycle counter, and a storage and transmission unit coupled to the measuring unit and that stores the measurement data obtained by the measuring unit and communicates the measurement data obtained by the measuring unit and stored in the storage and transmission unit, and a monitoring center positioned away from the cable railway and coupled to the storage and transmission unit by at least one data communications network, the monitoring center comprising:

an assessment and visualization unit that receives from the storage and transmission unit, via the at least one data communications network, the measurement data obtained by the measurement unit and stored in the storage and transmission unit, the assessment unit being provided with the number of splicing points and the known cable length and assessing the measurement data received from the storage and transmission unit including a number of bending cycles counted by the bending cycle counter and the number of splicing points and known cable length to provide a forecast of a life span of the cable and a life span of each splicing point and enabling visualization of the measurement data received from the storage and transmission unit.

2. The inspection and monitoring system according to claim 1, wherein the at least one data communications network uses Ethernet.

3. The inspection and monitoring system according to claim 1, wherein the measuring unit includes a magnetization unit that magnetizes the cable.

4. The inspection and monitoring system according to claim 1, wherein the measuring unit is configured to measure at least one of acoustic values and vibrations of the cable when moving to enable each of the least one splicing point of the cable to be located or detected.

5. A method of operating a cable railway comprising an inspection and monitoring system according to claim 1, the method comprising determining an operating state of the cable by online testing of the cable with electromagnetic signals.

6. The method according to claim 5, further comprising assessing inspection results taking into account parameters that influence the operating state of the cable.

7. The method according to claim 6, wherein the parameters that influence the operating state of the cable are selected from a group consisting of a number of bending cycles and a length of the cable path covered.

8. The method according to claim 5, wherein the assessment of test results additionally takes into account environmental conditions.

9. The method according to claim 8, wherein the environmental conditions are selected from a group consisting of ambient temperature in the system, lay length of the cable, noise emission of the system and a change in position of the tensioning carriage re-tensioning the cable.

10. The method according to claim 5, wherein the inspection and assessment process is carried out automatically according to a previously determined monitoring program.

11. The method according to claim 10, wherein the inspection process is initiated automatically by the monitoring program with a pre-specified frequency and/or at a pre-specified date.

12. The method according to claim 5, further comprising performing emergency stoppage of the cable railway when the measuring unit touches the cable or the measuring unit is damaged.

13. The method according to claim 5, further comprising initiating the measurement manually on the measuring unit or manually by means of the assessment unit each time there is remote access via a data connection/network connection.

14. The method according to claim 5, wherein the assessment unit enables automatic or semi-automatic assessment of the state of the cable and a life span forecast is generated from the assessment of the state of the cable.

15. The method according to claim 5, wherein remote access to the inspection and monitoring system is achieved with the aid of the assessment unit and the inspection and monitoring system is configured and updated in this way.

16. The method according to claim 5, wherein the test method detects lay length of the cable.

17. The inspection and monitoring system according to claim 1, wherein the storage and transmission unit includes a port that receives a USB stick.

18. The inspection and monitoring system according to claim 1, wherein the storage and transmission unit is configured to store a number of complete measurements of the cable and retain data in the event of a power failure.

19. The inspection and monitoring system according to claim 1, wherein the storage and transmission unit communicates the measurement data obtained by the measuring unit and stored in the storage and transmission unit wirelessly using a radio connection.

* * * * *